(12) United States Patent
Peloza et al.

(10) Patent No.: US 8,586,870 B2
(45) Date of Patent: Nov. 19, 2013

(54) MICROELECTRONIC COMPONENT SUPPORT WITH REINFORCED STRUCTURE

(75) Inventors: Kirk B. Peloza, Naperville, IL (US); John Dolaz, Spring Grove, IL (US)

(73) Assignee: Molex Incorporated, Lisle, IL (US)

( * ) Notice: Subject to any disclaimer, the term of this patent is extended or adjusted under 35 U.S.C. 154(b) by 687 days.

(21) Appl. No.: 12/732,883

(22) Filed: Mar. 26, 2010

(65) Prior Publication Data

US 2010/0243844 A1    Sep. 30, 2010

Related U.S. Application Data

(60) Provisional application No. 61/164,217, filed on Mar. 27, 2009.

(51) Int. Cl.
*H05K 1/03* (2006.01)
*H05K 5/00* (2006.01)
*H05K 7/00* (2006.01)

(52) U.S. Cl.
USPC ............ 174/255; 174/260; 361/752; 361/760

(58) Field of Classification Search
None
See application file for complete search history.

(56) References Cited

U.S. PATENT DOCUMENTS

| | | | | |
|---|---|---|---|---|
| 5,055,637 A | * | 10/1991 | Hagner | 174/260 |
| 6,663,946 B2 | * | 12/2003 | Seri et al. | 428/209 |
| 6,803,527 B2 | * | 10/2004 | Dishongh et al. | 174/260 |

* cited by examiner

*Primary Examiner* — Jayprakash N Gandhi
*Assistant Examiner* — Dion Ferguson
(74) *Attorney, Agent, or Firm* — Stephen L. Sheldon

(57) ABSTRACT

A microelectronic support assembly has a support member formed from plateable resin, such as liquid crystalline polymer and the support member is configured with a laser to define holes in the support member. These holes and other areas of the support member are plated and the plating forms a plurality of hollow metal columns that provide reinforcement to the support member so that it can resist wire bonding pressures.

14 Claims, 16 Drawing Sheets

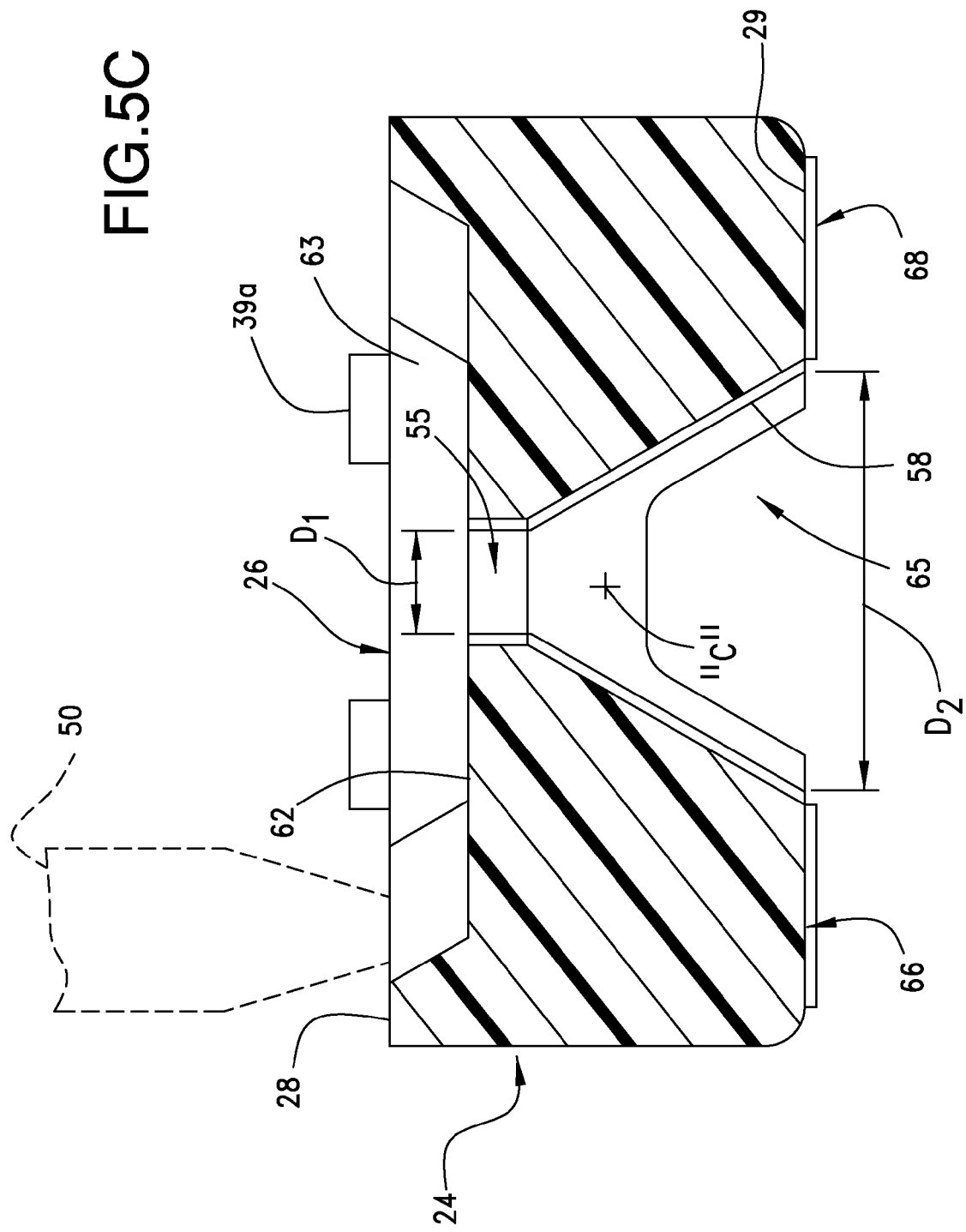

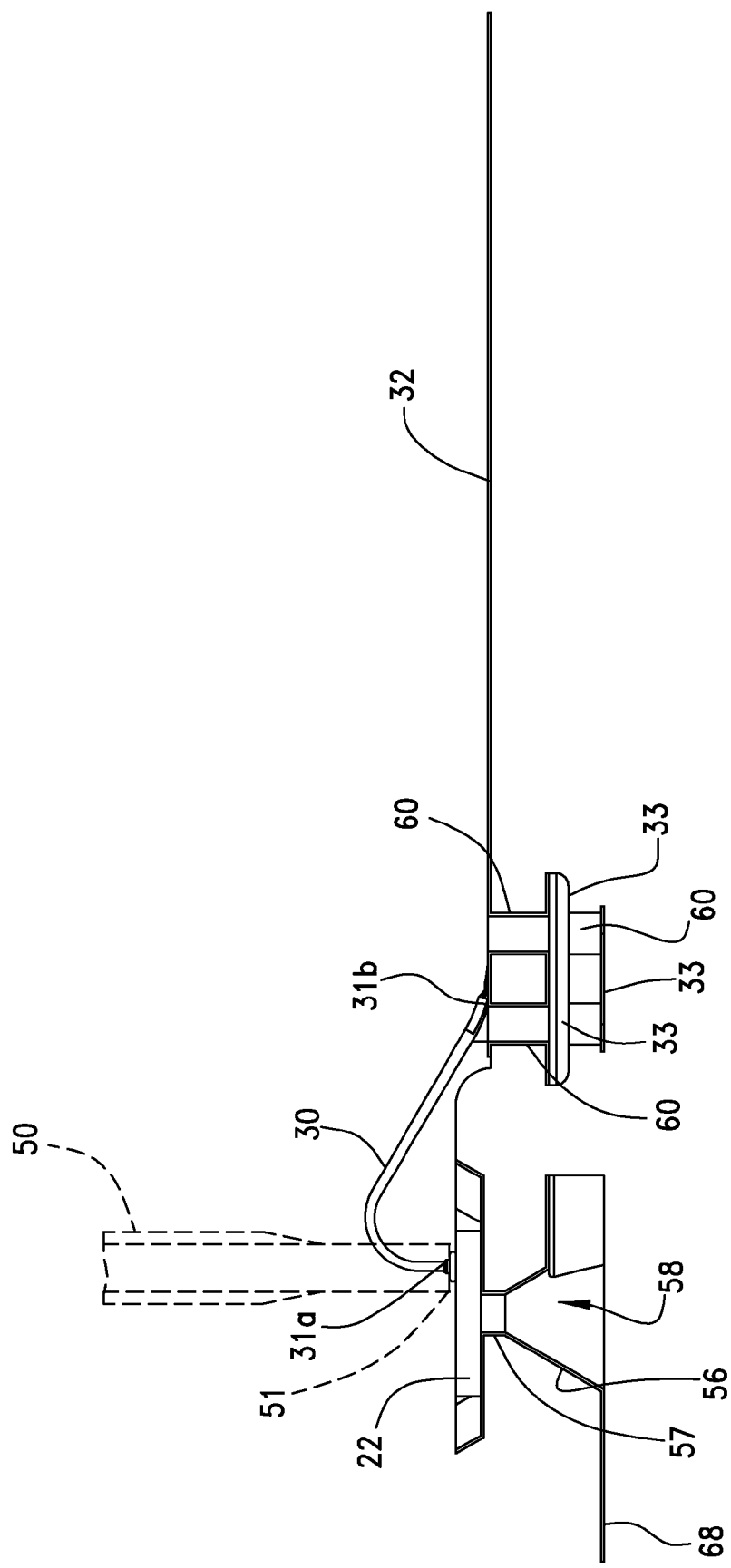

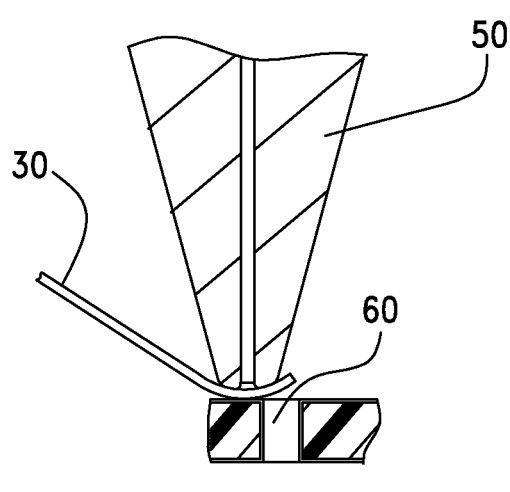
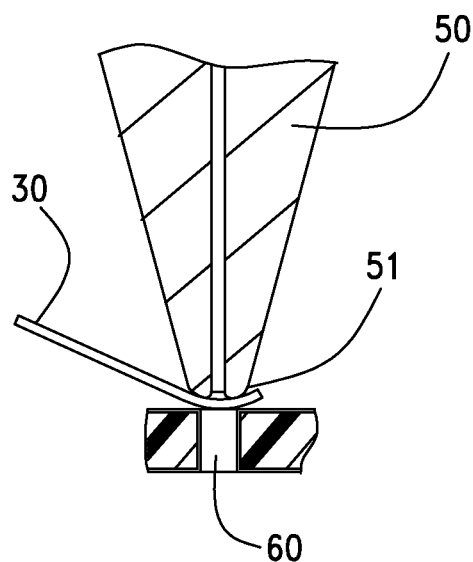
FIG.12A
FIG.12B
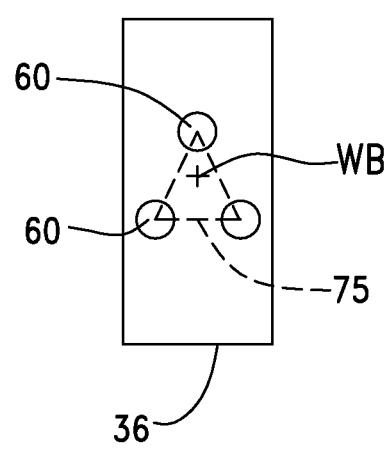
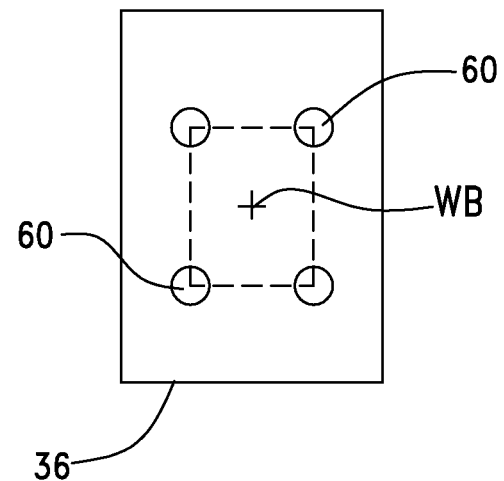
FIG.13A
FIG.13B

MICROELECTRONIC COMPONENT SUPPORT WITH REINFORCED STRUCTURE

This application claims priority to U.S. Provisional Application No. 61/164,217, filed Mar. 27, 2009, which is incorporated herein by reference in its entirety.

BACKGROUND OF THE INVENTION

1. Field of the Invention

The present invention relates generally to a support, and more particularly, to an improved support member for supporting a component.

2. Description of Related Art

There is a constant trend to reduce the size of devices in the electronics industry. This trend carries over into ancillary industries that are using more and more electronic devices. One such example is the medical equipment industry, where a premium is placed on microelectronic devices that are used in invasive applications, i.e., devices which are inserted into the human body. These medical devices need to be very small out of necessity, given the size of body passages and many of them are used to monitor active body conditions and hence include one or more sensors.

In medical and other applications, one type of integrated circuit is known as microelectronic mechanical system ("MEMS") and sensors made of MEMS can be used for monitoring pressures, status, environmental conditions and other parameters. Integrated circuit sensors, such as MEMS sensors, can be made relatively small and thus they can fit within the sensing tip mentioned above. Typically a sensor needs to be attached to a support member and interconnected with wires, which often are connected to conductive traces to which other conductive leads may be attached for receiving and transmitting signals from the sensor to an receiving device. Wire bonding is the form of attachment commonly used in microelectronics to interconnect integrated circuits to circuit board substrates. Wire bonding can also be used to connect microelectronic devices to other elements. Such bonding involves the application of heat and pressure, and sometimes ultrasonic energy to a substrate or element and a wire to form a bond between the two. Due to the pressures involved in wire bonding, however, the material chosen for the support member must have a relatively high compressive strength in order to resist deformation imparted to the support member by the bonding tool during the bonding process. FR4 is a material that is commonly used in the manufacture of printed circuit boards. It can be used as a support member for a variety of electrical components, such as MEMS, and FR4 has a relatively high compressive strength that resists deformation under the pressure of wire bonding. However, FR4 is formed from woven glass which is encapsulated in an epoxy resin and it is difficult to form into complex shapes. Furthermore, depending on the application, FR4 may not be sufficiently biocompatible and FR4 cannot be easily machined to obtain a smooth surface, especially in the miniature environment of the aforementioned devices where the support is about 1 or less mm in thickness, because the material tends to flake when worked, which can lead to coplanarity issues.

Thus other less rigid materials must be used to support these microelectronic devices, particularly in applications where biocompatibility is desired. A material such as a liquid crystalline polymer (LCP) is available in biocompatible formations and can be readily formed and/or machined to provide complex shapes. However, the use of a material having compressive strengths that is significantly lower than a material like FR4 may lead to deformation of the support member, which may affect the operational characteristics of the microelectronic device.

Accordingly, certain individual would appreciate an improved support member that can be used in microelectronic applications.

SUMMARY OF THE INVENTION

In an embodiment, a microelectronic device support assembly may include an elongated carrier, a recess for receiving a microelectronic device, a microelectronic device supported by the carrier, and a plurality of conductive traces disposed on the carrier that are spaced apart from the microelectronic device and which are interconnected to the microelectronic device by a plurality of wires, the carrier being reinforced by separate metal layers applied proximate to the area of attachment of the wires to the traces. The carrier may be formed from a moldable resin having a relatively low compressive strength, such as liquid crystalline polymer (LCP). The carrier can include a first area that supports a microelectronics device, and a second area with a conductive trace disposed thereon running along a surface of the carrier so as to define a termination area for the microelectronic device. The support can further include a conductor terminated to the microelectronic device and the conductive trace. The carrier can be reinforced by a plurality of metal layers disposed on selected surfaces of the carrier and can include a hole formed therein that extends between two surfaces of the carrier. The hole can be disposed proximate to the wire-terminations areas of the carrier and the hole is plated so as to provide a reinforcement column extending through the carrier, the column configured to provide resistance to pressure applied during termination of the wires to the carrier.

In an embodiment, the aforementioned hole in the carrier may be formed by using a laser to drill, or etch the hole in the body of the carrier. The carrier can be formed from a material such as a LCP that is rendered plateable after contact by the laser. When the hole in the carrier is plated with a conductive plating solution so as to define a column, the column helps provide reinforcement to the support carrier in that location.

BRIEF DESCRIPTION OF THE DRAWINGS

During the course of the following detailed description, reference will be made to the following drawings in which like reference numbers identify like parts and in which:

FIG. 5C is a sectional view of the support carrier of FIG. 5A, taken along lines C-C thereof;

FIG. 6 is a cross-sectional view of FIG. 4, taken along lines 6-6 thereof;

FIG. 12A is a diagrammatic view of an alternate embodiment of the present invention, utilizing a single reinforcing column;

FIG. 12B is the same view as FIG. 12A, but illustrating the wire bonding location as directly over and in contact with the reinforcing column;

FIG. 13A is a top plan, diagrammatic view of a conductive trace of a support carrier illustrating an alternate embodiment of a reinforcing column pattern, using three columns and the wire bonding are located within the three columns; and FIG. 13B is another top plan diagrammatic view of an alternate reinforcing column utilizing four columns surrounding the wire bonding attachment area.

DETAILED DESCRIPTION

Figure 1:
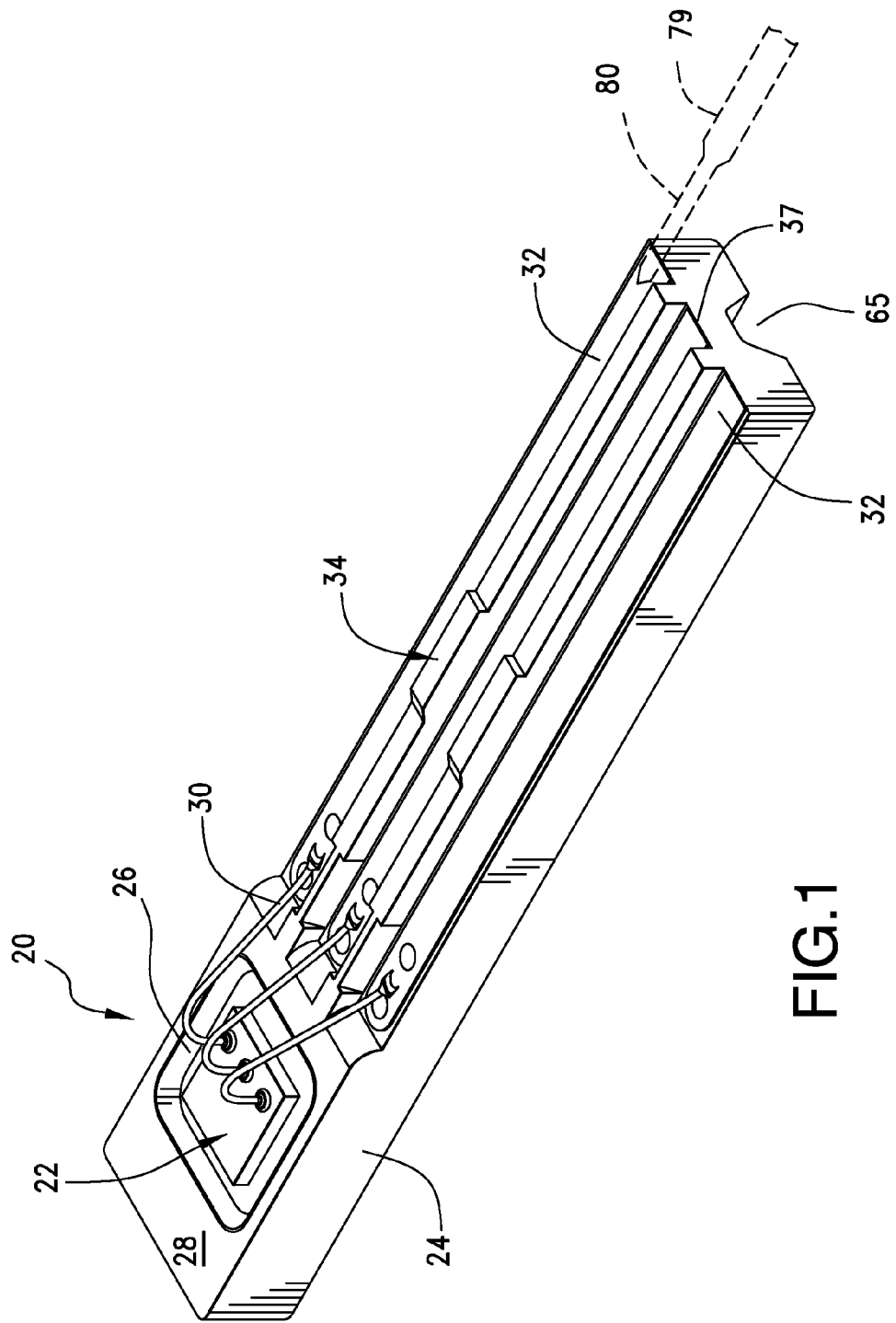
FIG. 1 is a perspective view of an embodiment of a electronic component support assembly that includes a support carrier.
Figure 2:
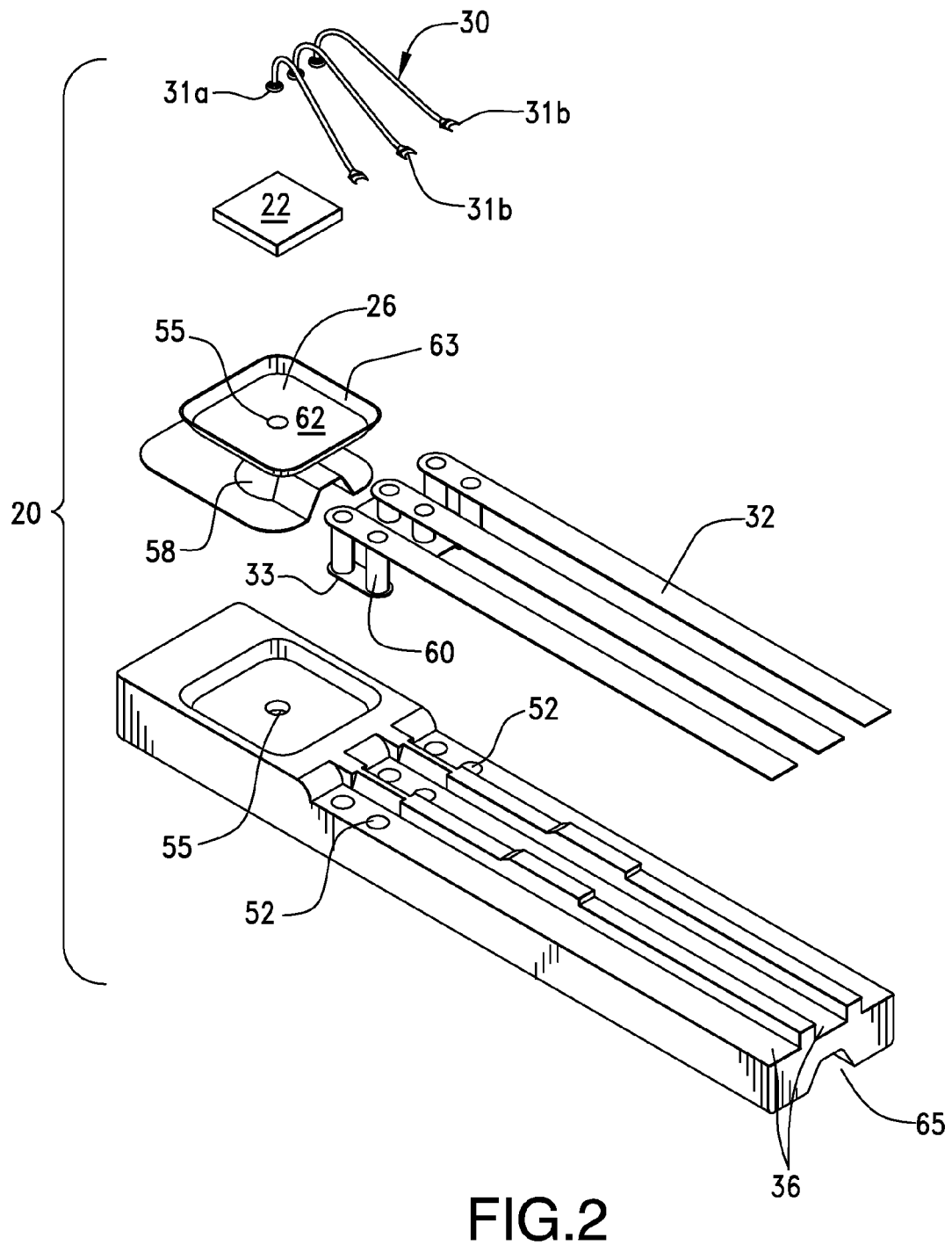
FIG. 2 is an exploded view of the support assembly of FIG. 1.
Figure 3:
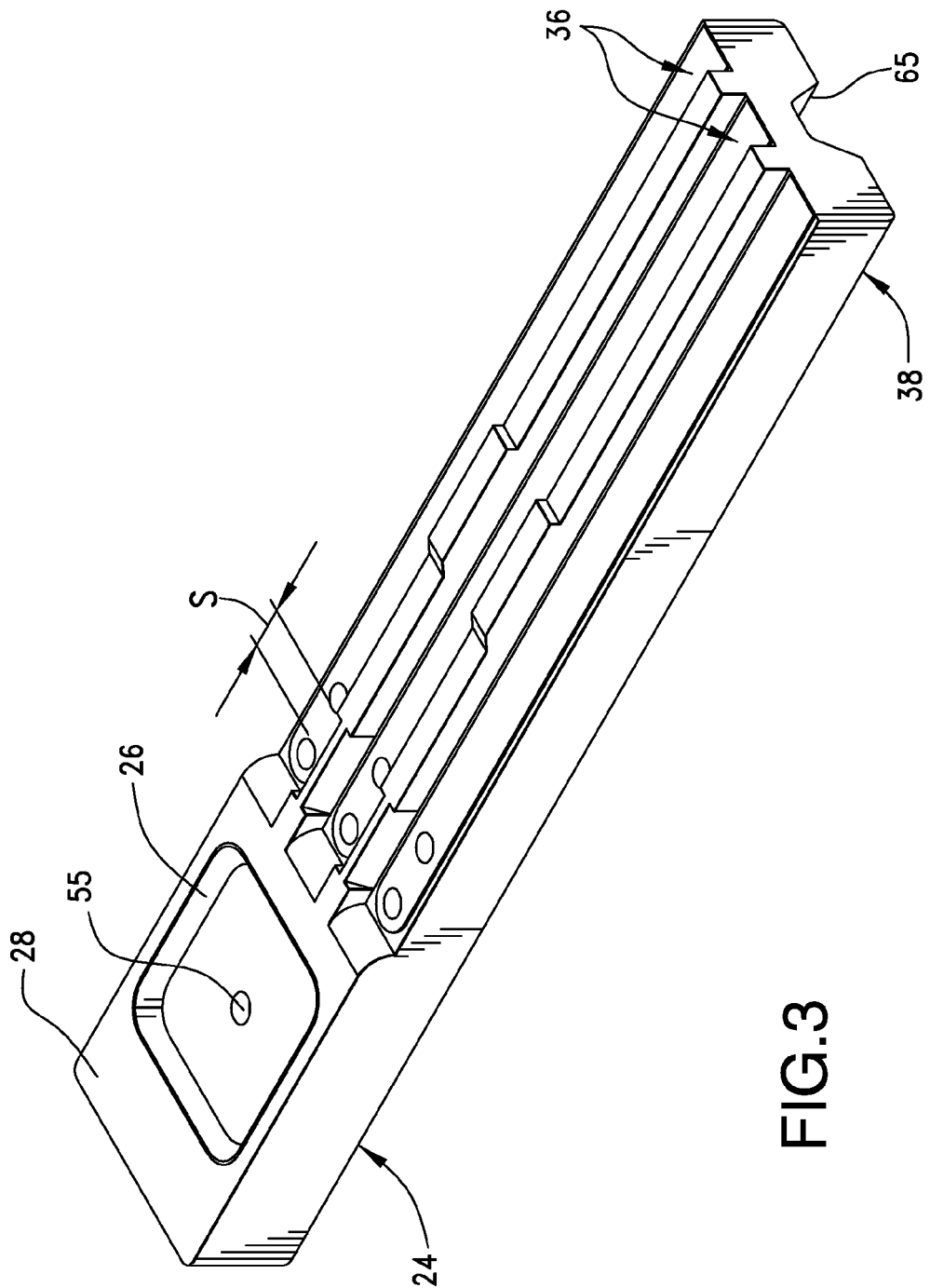
FIG. 3 is the same view as FIG. 1, but with the MEMS and wires removed for clarity.

Before discussing the features depicted in the figures, several embodiments can be discussed in general terms. It should be noted that the features described and illustrated herein can be used different configurations, depending on the application. Therefore, specific details disclosed herein are not to be interpreted as limiting, but merely as a basis for the claims and as a representative basis for teaching one skilled in the art to variously employ the present invention in virtually any appropriate manner, including employing various features disclosed herein in combinations that might not be explicitly disclosed herein.

In general, a carrier with one or more support holes may plate additional areas in the form of horizontal traces that are preferably disposed on the top and bottom surfaces of the support carrier, these conductive traces being interconnected by the plated columns so as to provide a conductive path along and through the support carrier. Furthermore, the traces can be disposed within one or more channels that are formed on one surface of the support carrier where the channels defining wire termination locations for free ends of external wires. If desired, the channels being separated from each other by raised ribs that protect the traces in the channels form abrasion during the plating process.

In an embodiment, a plurality of holes may be provided in the body of the support carrier. For example, a pair of holes can be associated with a single internal wire leading from the microelectronic device, and the holes can be spaced apart from each other by a predetermined distance so as to define a bonding area where the free end of the internal wire is bonded to a conductive trace. To provide support, the holes can be plated with a metal layer to form hollow columns that extend vertically through the support member, the columns providing support to the support carrier during wire bonding. As can be appreciated, the exterior of the columns is surrounded by the support carrier, which provides additional support that helps prevent the columns from buckling.

In an embodiment, a reinforcement to the support carrier can be provided in the first area where the microelectronics device is attached to the support carrier by providing a well, or recess in a first, preferably top surface of the support carrier, the well being plated with a metal to thereby provide a suitable attachment between the support carrier and the microelectronic device, the support carrier further including a support structure positioned below the well. The support structure may comprise a hollow conical opening formed in a bottom surface thereof, the conical opening extending upwardly within the support carrier and into contact with the well, the conical opening also being plated so as to define a hollow metal support in the body of the support carrier and extending beneath the support well, the conical opening having a first diameter that communicates with the recess and a second diameter which is larger than the first diameter, which communicates with a base extending around the bottom of the conical opening, the interior surface of the conical opening being plated with a metal layer to form a frusto-conical metal support element embedded in the support carrier.

As can be appreciated, a carrier may include a hollow metal element disposed beneath the recess with a relatively large, and substantially planar plated metal area interconnected to the conical element and which is sufficiently large enough to provide a flat base that extends for almost the full width of the support carrier to provide rigidity to the support carrier and resistance to torque forces developed during wire bonding, especially in applications where the bonding tool contacts the support carrier at a location offset from a centerline of the support carrier.

In one embodiment, a microelectronics support assembly includes a support carrier with an elongated support member that is formed from a material that can be rendered plateable by excitement thereof with a laser. One such material is liquid crystalline polymer ("LCP"), which may be the RTP Company 3499-3X113393A laser direct structuring ("LDS") compound. The support member has a support area defined thereon in the form of a recess, that serves as a well, or pan, and which receives a microelectronic device therein, such as a MEMS sensor. The support member may further provided with a plurality of horizontal grooves that define channels which will receive the ends of signal transmission wires that are terminated to the carrier, and which lead to a display or other similar instrument. The grooves may be bounded by raised ribs. The microelectronic device is terminated to the conductive traces. To support the termination process, which may be accomplished through wire bonding, a support structure is provided under the area of termination. In an embodiment, the support structure may be one or more columns; other support shapes, however, may be used. The support structure provides additional structural strength to the force applied during termination. It should be noted that the support structure may be configured so that it might be prone to buckling. The support structure, however, can use the material it is reinforcing (e.g., the LCP) to help prevent the occurrence of buckling. In the case of the use of columns, the column(s) can be restrained from buckling outward by the body of the support member which surrounds them, so that the plating that define the column serves to reinforce the support carrier and lessen the likelihood of the support carrier incurring any significant deformation during bonding.

In an embodiment, a pair of columns may be used to support each termination. It should be noted that a single column may be used and in such an application the termination may occur directly to the column or the column may be disposed so that it is adjacent the termination area. In a further embodiment, more than two columns may be used to reinforce the termination area.

In an embodiment, the support area for the microelectronic device may be reinforced. A first recess may be formed on one surface of the carrier that defines what may be considered as a pan or a well. The microelectronic device is received within the first recess and a second recess is formed on the bottom surface of the support member, in opposition to and in communication with the first recess. The two recesses are interconnected by an opening that is formed in the first recess carrier and which extends vertically between the first and second recesses. These two recesses can be formed with a laser and all of their surfaces, including the intervening communicating hole, may be plated with metal. The metal plating layer in the first recess provides a metal base to which the microelectronic device may be attached such as by soldering or the like, and the opening that extends through to the second recess forms a passage that may be aligned with a pressure transducer on the microelectronic device. The second recess is aligned with the first opening and is disposed underneath it, and it communicates with a channel, or slot, formed in the underside of the support member that extends the length of the support member.

The second recess can have a tapered, potentially frustoconical, configuration with a first, smaller sized portion at a first end and a second, larger size at its second end. The second recess can be positioned generally centrally beneath the first recess so as to provide a cone-shaped support element when plated. As can be appreciated, the second recess can help resist pressure applied when the wires are terminated to the microelectronic device. It should be noted that the second recess, while it may be a cone-shaped structure, may also include additional, more complex shapes such as slots extending in a desired direction. Such a slot communicates with the frusto-conical element and can take the form of a truncated, inverted V-shape channel that extends for a selected distance lengthwise along the bottom surface of the carrier body. This V-shaped passage also provides, when plated, a metal support element that is positioned under the edge of the microelectronic device where the termination takes place. Other shapes may also be provided.

Thus, as can be appreciated, an additional plated portion may be disposed on the bottom surface of the support member directly underneath the support structure. This plated portion can form a metal layer that may be generally planar and can extend beneath the termination point and even substantially the entire width of the carrier. This plated portion can serve as an anchor plate that assists in counteracting the termination pressure forces that are developed in the support member body when, for example, bonding wires to the microelectronic device and to the conductive traces. In an embodiment, the plated portion extends under the portion of the support member that is subject to the termination pressure and provides resistance to torque if the termination pressure is applied at a location offset from a centerline of the support member.

Turning to the figures, a reduced size electronic component support assembly 20 is depicted. The assembly 20 is elongated and it supports a microelectronic device such as a MEMS 22 (microelectronic mechanical system) or integrated circuit (IC). A MEMS is used herein as an example only because it is a device commonly used in pressure sensing application, but it will be understood that the microelectronic device is not limited to a MEMS and may include any type of sensor, IC chip, solid state chip or similarly-sized devices.

The microelectronic device 22 has a chip-like configuration and typically may have dimensions of about less than 1.0 mm by 1.0 mm. The thickness of the MEMS is also very small, typically being less than about 1 mm. The MEMS 22 is disposed on a substrate, or elongated support member, or carrier, 24 that has a well or recess 26 formed in a top surface 28 thereof. The support member 24 is also referred to herein as a "carrier" in that it holds the microelectronic device in place with other components such as wires and traces as an integral unit. The MEMS 22 further includes a plurality of wires, or conductive leads 30 that interconnect segments of the MEMS with a like plurality of conductive traces or paths 32 that are disposed on an adjacent surface 34 of the support carrier 24. The microelectronic device 22 is typically intended to be used in a component that is miniature, such as, for example, an invasive pressure sensor that is encompassed within a housing about 7 to 8 mm in length and about 2 mm or less high. As such, the thickness of the support carrier 24 is very small, between about 0.6 to 0.7 mm.

The adjacent surface 34 of the support carrier 24 may be grooved as shown and the traces 32 disposed within and extending along the bottom wall, or floor of each such groove 36. The two opposing ends 31a, 31b of the wires 340 are joined; respectively to the MEMS 22 and the conductive traces 32, preferably near the distal ends thereof. The traces 32 run the length of the support carrier 24 to the proximal end 38 of the support carrier 24. As noted above, these traces 32 are disposed in grooves 36 which are flanked by raised walls, or ribs 39. The grooves 36 accommodate ends of wires (not shown) that are connected to the traced 32 and which lead to other components such as scopes, displays and the like. Hence the grooved area of the support member may be considered as a wire termination area, receiving not only the ends 31b of wires 32, but also the free ends 80 of wires 80 (FIG. 1) that serve to connect the microelectronic device to a display, scope or similar component.

Figure 10:
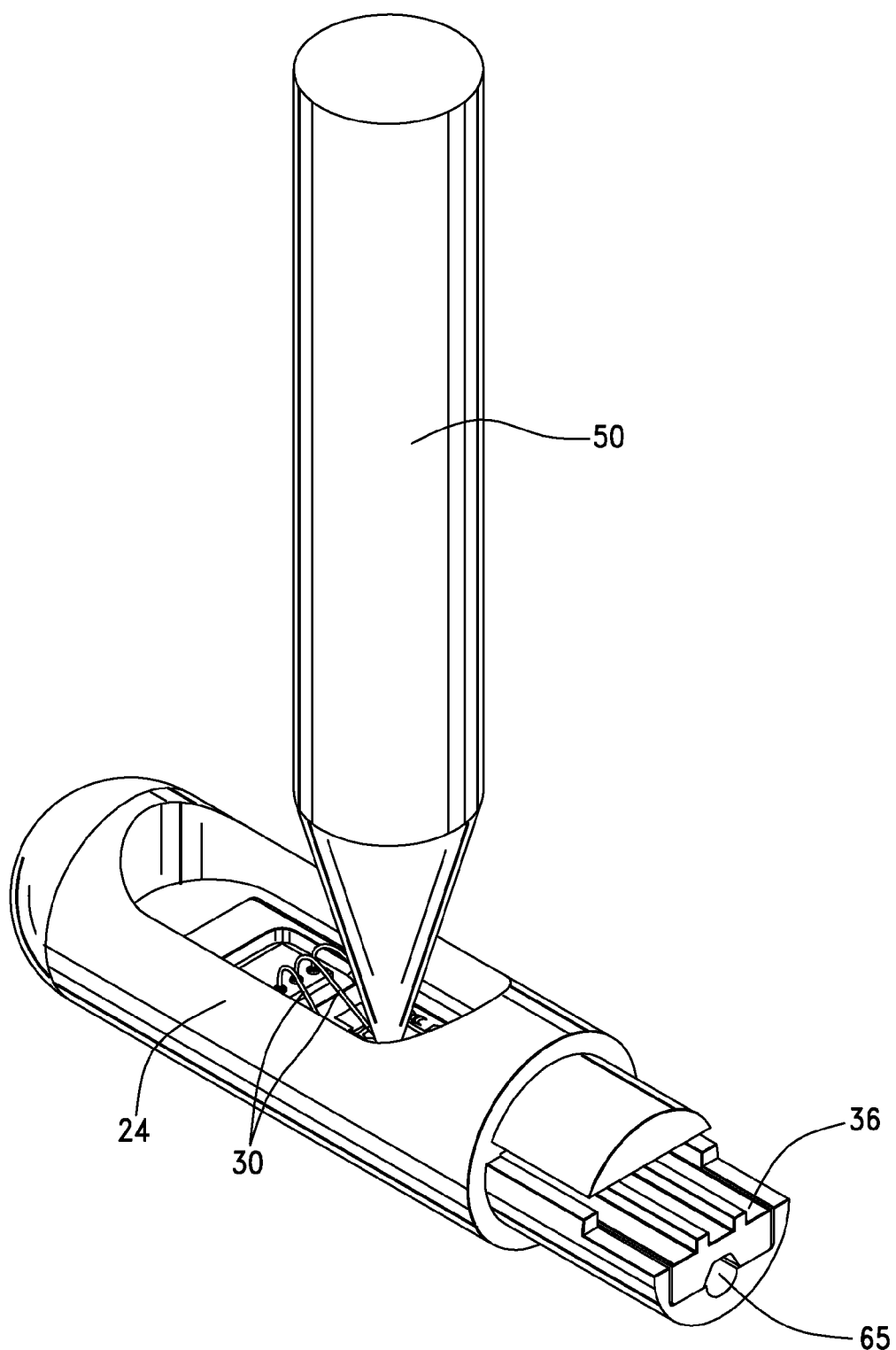
FIG. 10 is a perspective view of the support assembly of FIG. 1 disposed in place within an enclosure.
Figure 11:
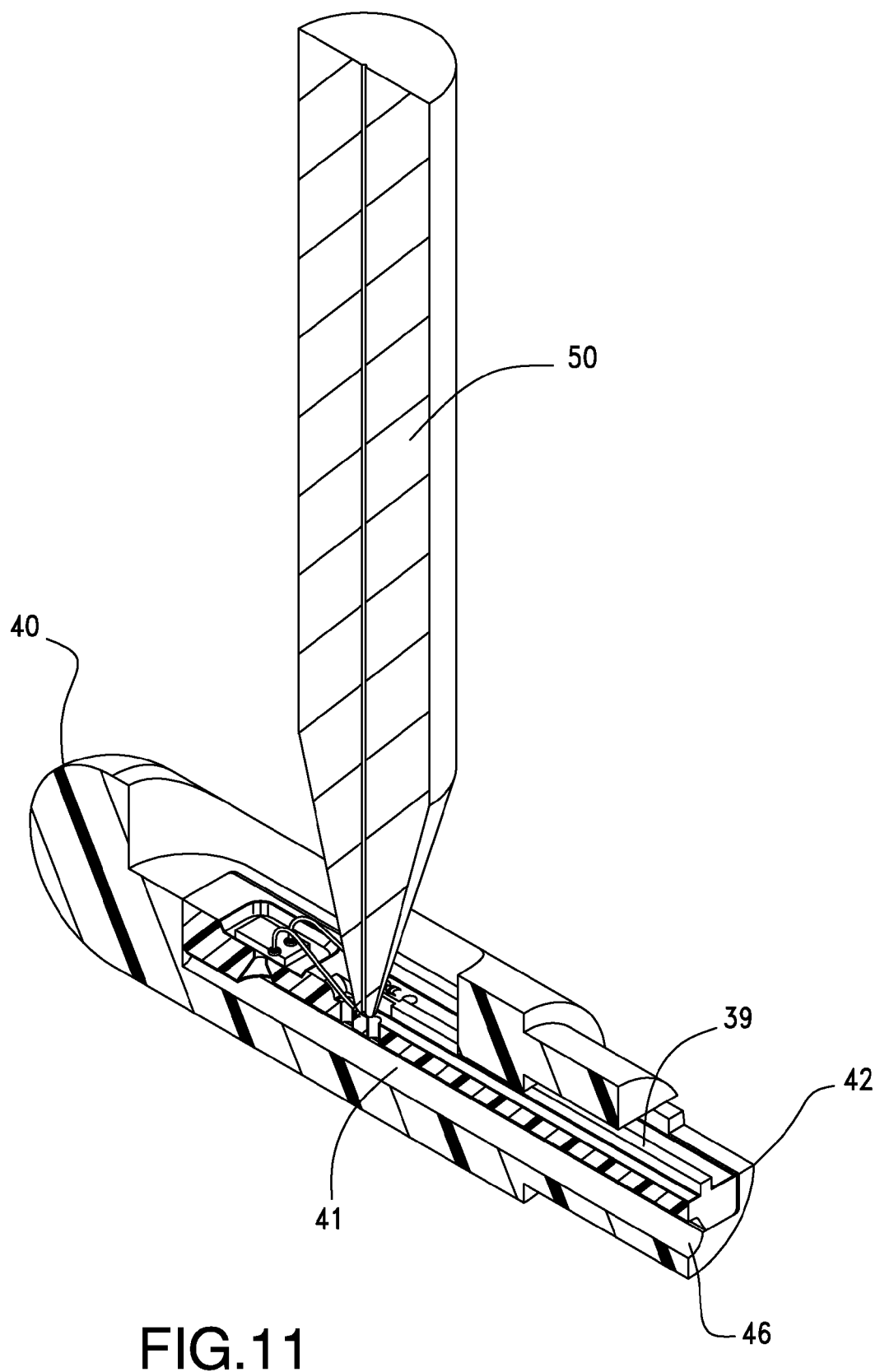
FIG. 11 is a cross-sectional view of FIG. 10.

In an embodiment, the MEMS 22 may be a differential pressure sensor or a sugar monitor, and due to its small size, may be incorporated into a catheter. Such an application is generally illustrated in FIGS. 10 and 11, wherein the support assembly 20 is shown enclosed within the housing 40 of a catheter. The housing 40 is hollow, and defines an internal enclosure 41 into which the support carrier 24 may be inserted. The grooves 36 of the support carrier 24 are open at the rear 42 of the housing 40 for the insertion of wire ends 80 therein. As noted above the particular medical environment in which the present invention may be used is extremely small, with the MEMS being approximately 1 mm square and less than 1 mm thick, while its supporting carrier may having general dimensions of about 5 to 6 mm long by less than about 2 mm wide, and less than about 1 mm thick. As such, both the MEMS and its supporting carrier are susceptible to deformation during assembly. Care must be taken to maintain tolerances and dimensions for insertion of the support carrier into a housing of a component.

In order to provide a useful connection in microelectronic applications, the preferred manner of attaching the wire free ends 31a, 31b to the microelectronic device 22 and the conductive traces 32 is by a wire bonding method. Wire bonding involves the use of a bonding tool 50 that applies thermal and sometimes ultrasonic energy under pressure to form an effective bond. The tip 51 of the bonding tool 50 is pressed against the wire end 31a, 31b and heat and pressure is applied to the wire end and the surface supporting it. Due to the pressure that is required in wire bonding, the application of wire bonding is typically limited to certain materials that are used as the support members, such as FR4, which is commonly used in the manufacture of printed circuit bonds. FR4 is a glass/epoxy phenolic that uses a woven fiberglass fabric with an epoxy resin. FR4 has a high compressive strength of about 55,000 psi (about 380 MPa) in half-inch thickness. However, due to the woven glass fabric used in FR4 it is difficult to shape, or cut wells, grooves and other patterns for components having dimensions such as a few millimeters or less. Thus, its use in microelectronic applications is limited.

In an embodiment, however, LCP (liquid crystalline polymer) can be used in the fabrication of support assemblies as shown in the drawings. LCP exhibits acceptable temperature stability and can therefore survive the temperatures used in wire bonding, i.e., 300° C. to 500° C. However, it is well noted in the art that LCP exhibits very poor compressive strength, typically in the range of 20-30 MPa and plateable LCP tends to have even lower compressive strength. Even reinforced LCPs that are otherwise suitable for forming of complex shapes tend to have insufficient compressive strength, typically less than 100 MPa at 1% deflection. Thus, it is expected that reinforced plateable LCPs will typically have a compressive strength of less than 50 MPa at 1% deflection.

It has been discovered that the support carrier 24 can be formed from a low compressive strength, plateable resin, such as the RTP Company 3499-3X113393A LCP if the areas proximate to the wire bonding attachment locations are reinforced by plating selective areas of the support carrier. In particular, this reinforcement may be accomplished by exciting selective surfaces of the support carrier with a laser and subsequently plating these surfaces. The use of a laser in this fashion is known as LDS and it dispenses with the need to use two-shot molding for a plated device as has been done in the past. The LCP material is easily configured using a laser and finer details may be obtained thereby, without the flaking and other degradation that is prone to occur with materials such as FR4. Other plateable resins may also be used and these materials also have a low compressive strength as compared to the FR4 material.

Figure 4:
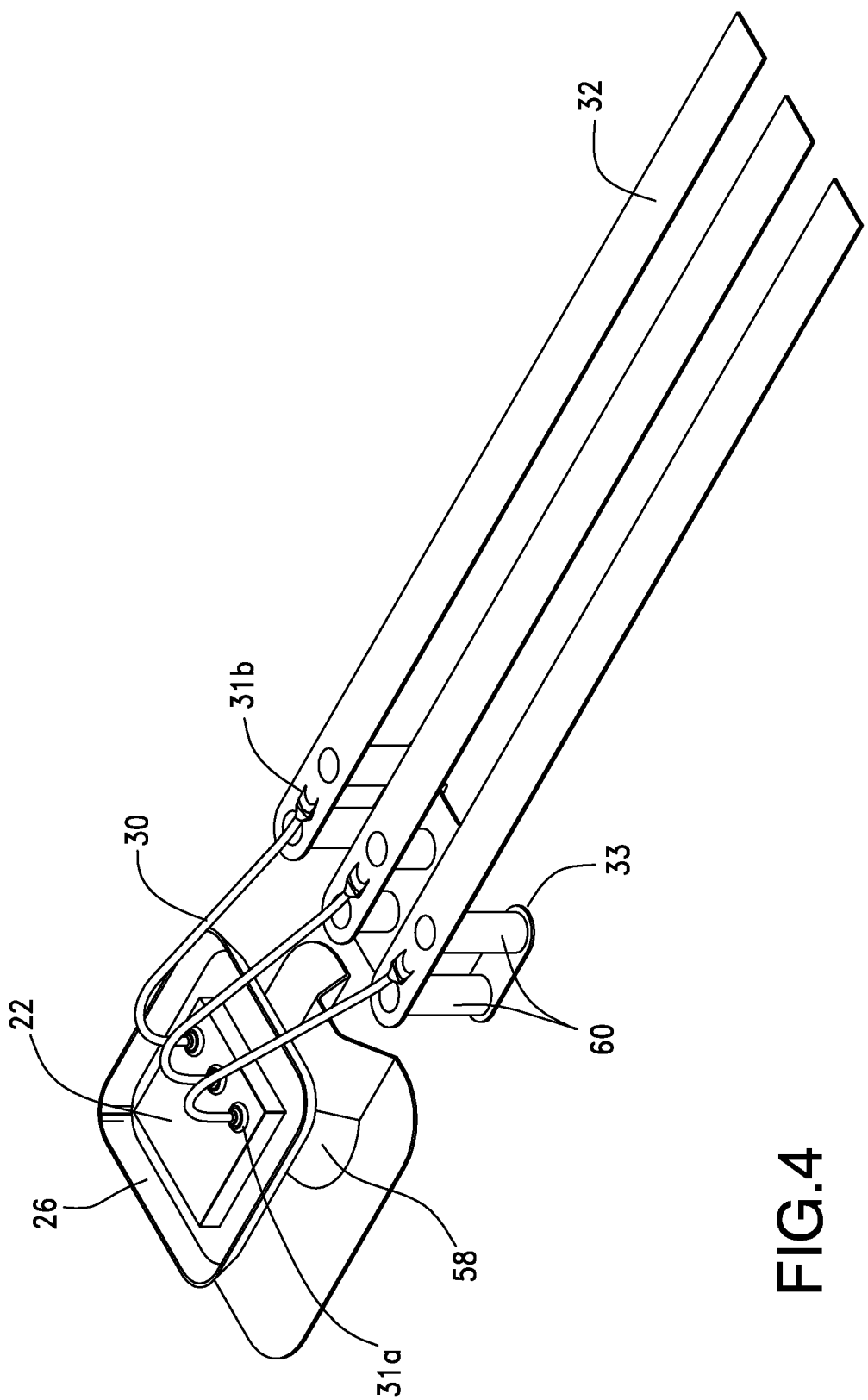
FIG. 4 is the same view as FIG. 1, but with the body of the support carrier removed for clarity, thereby illustrating the plated surfaces disposed on the support carrier.
Figure 5:
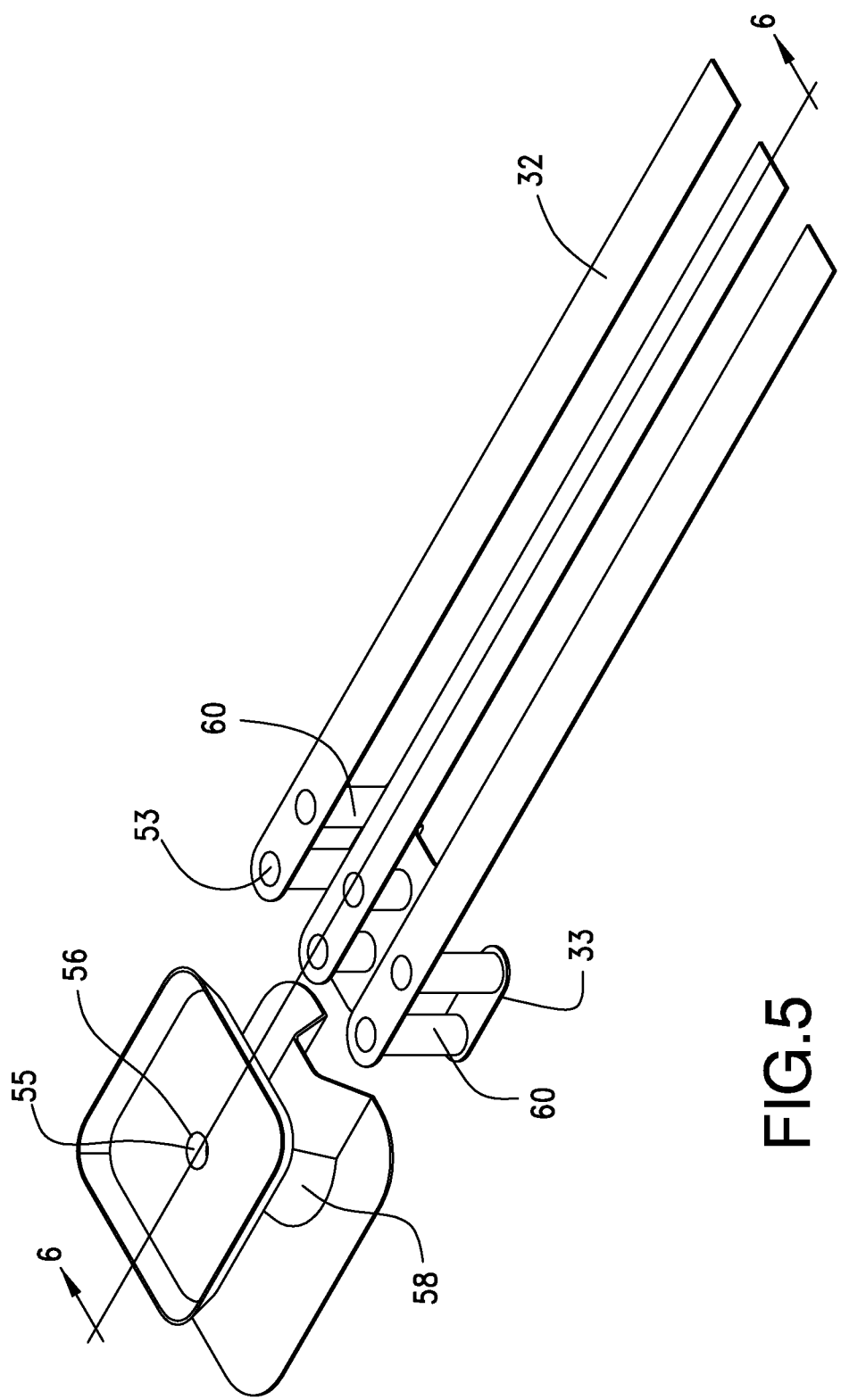
FIG. 5 is the same view as FIG. 4, with the MEMS and wires removed.
Figure 7:
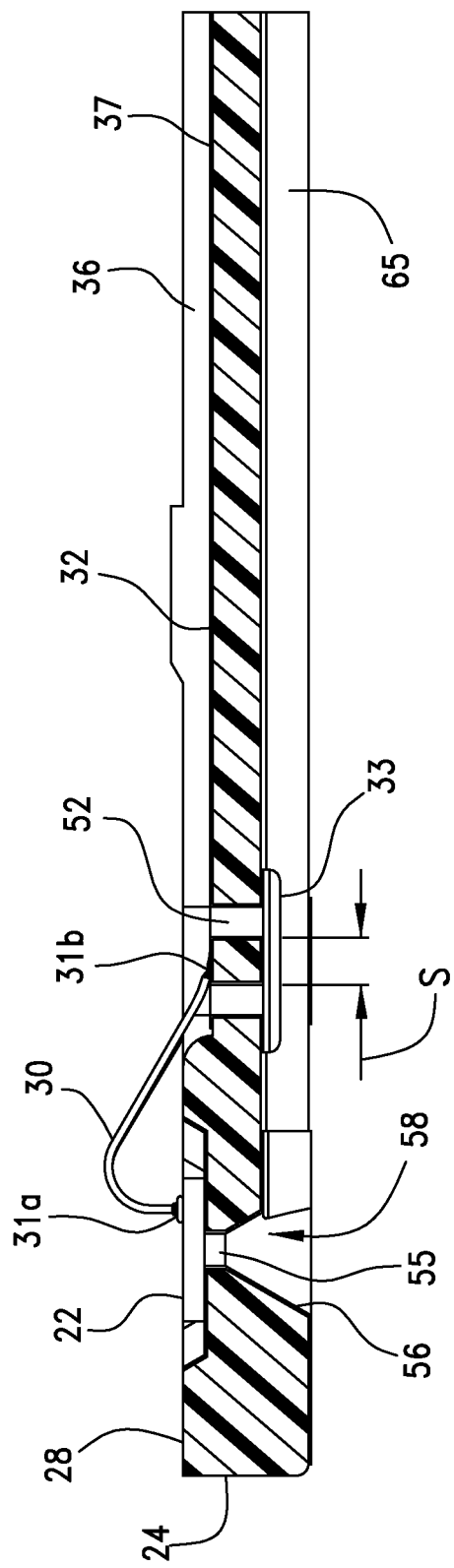
FIG. 7 is a cross-sectional view of FIG. 1, taken along lines 7-7 thereof.

FIG. 4 illustrates the plated areas of the support assembly 20 and the MEMS 22 and wires 30 separated from the support carrier 24, while FIG. 5 illustrates only the conductively plated areas. It can be seen that each such conductive trace 32 preferably has two reinforcement columns 60 that extend vertically through the support carrier 24 (FIG. 7) and which serve to interconnect top and bottom traces 32, 33, respectively. Once the desired surfaces of the support carrier 24 are excited with the laser, the support carrier 24 is immersed into an electrolyses plating solution and agitated so that the excited areas are plated with a conductive material that may include copper, nickel, palladium, silver and/or gold. This plated structure typically may include a plating thickness of between 2 to 15 microns of copper, 5 microns of nickel and a surface layer of about 1 to 2 microns of gold.

Figure 5A:
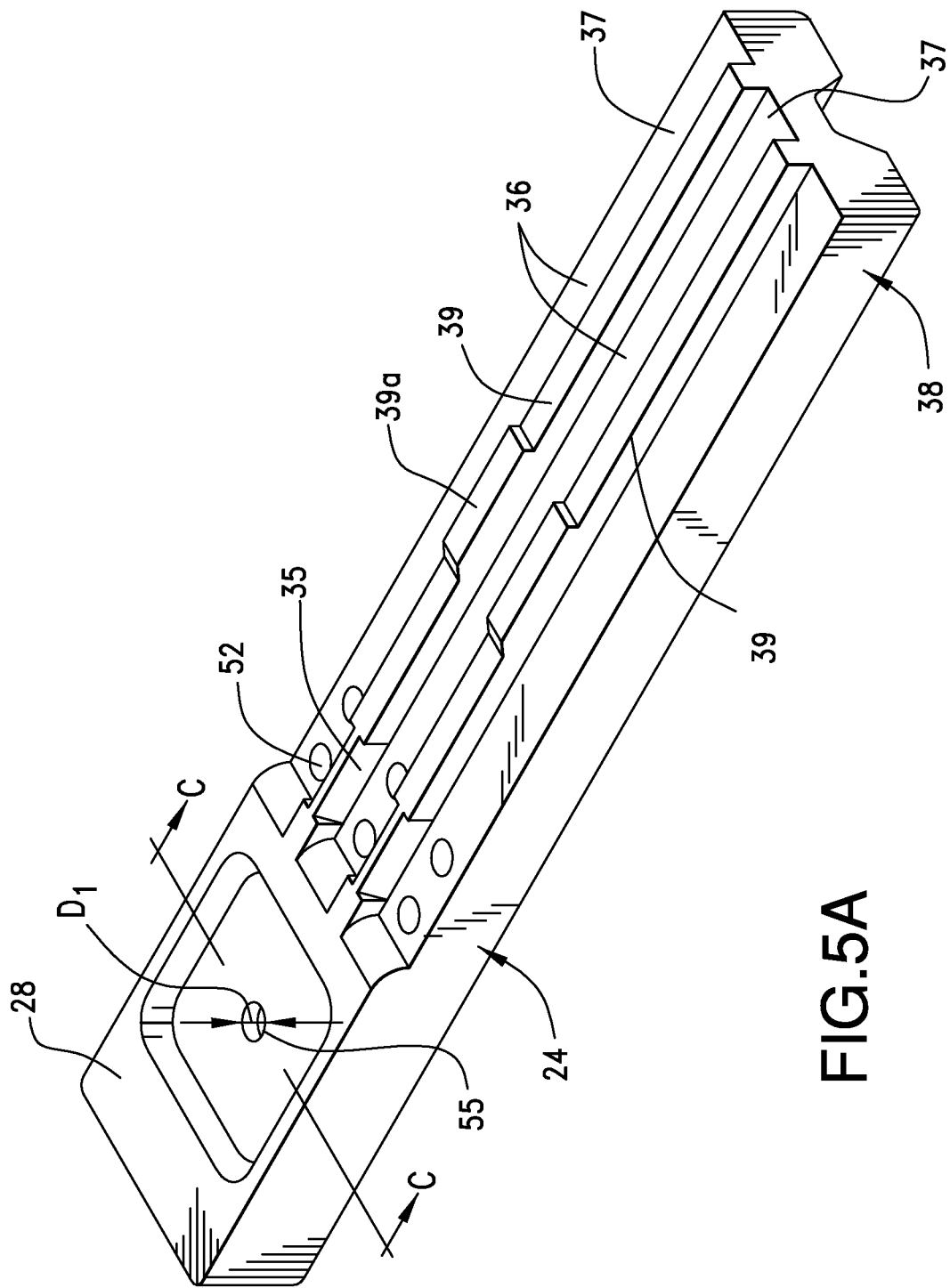
FIG. 5A is a perspective view of the support carrier of the support assembly with the conductive plates areas, the microelectronic device and the interconnecting wires removed for clarity.
Figure 5B:
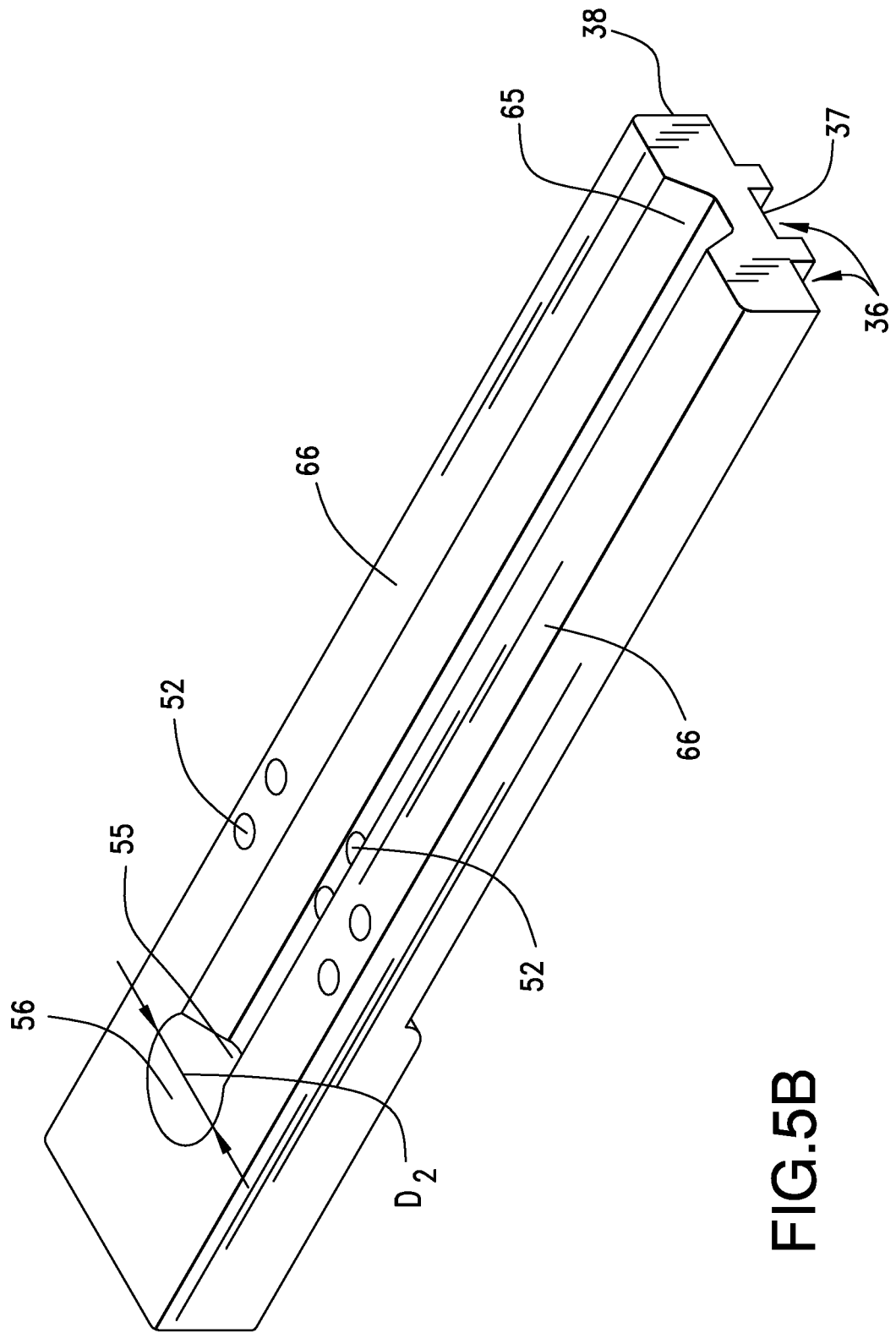
FIG. 5B is a perspective view of the underside of the support carrier of FIG. 5A.

As shown best in FIG. 5A the support carrier 24 and its particular configuration may be initially molded with the grooves 36 formed in place and the holes 52 may be subsequently formed with a laser. In the preferred embodiment illustrated, particularly in FIG. 7, the holes 52 spaced apart from each other a desired spacing 5 that is sufficient to receive the free ends 31b and provide a large enough area for wire bonding to be implemented there. This spacing 5 is an edge-to-edge spacing of the holes 52.

The holes 52 are drilled using the laser and the plastic from which the support member 24 is formed is rendered plateable by the laser drilling, as mentioned above. The interior surfaces 53 of the holes 52 are subsequently plated and the plating thereon defines a pair of columns 60 that extend preferably vertically through the support member and at least transverse to the longitudinal extent of the support member 24. It should be noted that the plating may be any desired plating and in an embodiment may be gold over electroless nickel over electroless copper, where the nickel substantially provides the structural reinforcement. These columns 60 provide structural reinforcement to the support member to help resist the pressure imparted by the bonding tool 50. Furthermore, the columns 60 may be considered as being embedded in the support carrier 24, for the support carrier completely surrounds the columns 60 and therefore provides resistance to any buckling of the columns 60, which is the common mode of structural failure with a column. In an embodiment, the columns may be oriented perpendicular with respect to the mounting surface of the carrier so they are aligned with the vertical pressure that is imparted to the support carrier during bonding to prevent unbalanced moments from occurring during assembly. However, it is contemplated that the columns may be slightly skewed within the pairs, i.e., the columns in the pairs are angled toward each other at their tops and spread outwardly at their bottoms. In finite element analysis modeling of the structure shown in the drawings the maximum worst case deformation was 0.024 mm, thus in a suitable supported structure no more than 5% total deformation would be experienced under forces that would be expected to be applied with wire-bonding. Therefore, the support member in combination with the structural reinforcement can provide a resultant support member that has four or five times and more preferably at least ten times more compressive strength at 1 percent deflection than the support member can provide without the structural reinforcement.

Although the columns 60 that are shown in the Figures are circular columns, they are not so limited. A cylindrical column is sometimes the most efficient configuration from a structural analysis viewpoint, but other column configurations may be used such as rectangular, square, triangular, ellipisoidal and the like. The ribs 39 that separate the grooves 36 may include chamfered portions 35 formed in their sidewalls in proximity to the reinforcing columns 60 in order to facilitate clearance for the bonding tool to reliably contact the wire end and the trace. Also, the ribs 39 may be provided with crush rib portions 39a that will provide an interference fit for the support member when it is inserted in a component housing 40 (FIG. 10).

Similarly, the area that supports the microelectronic device 22 is also reinforced by plated metal layers. The support recess 26, which may also be referred to as a support "pan" is first drilled, or laser etched into the top surface 28 of the support carrier 24 to form a preferably flat floor portion 62 that is surrounded by a sidewall 63 on its perimeter. The surfaces of the floor 62 and its sidewall 63 are plated and collectively define the recess 26 that receives the microelectronic device, or MEMS. As depicted, a hole 55 is formed that extends through the support carrier 24 and the hole 55 connects with a partially conical, preferably frusto-conical opening 56 formed in the bottom surface and portion of the support member 24. The hole 55 is plated to form a very small column 57 that interconnects the top recess 26 and the frusto-conical element 58 together. The frusto-conical element 58 begins with a small diameter, D1 (FIG. 5C) that begins with a diameter equal to that of the column 57 and which expands to a greater diameter, D2 that is the diameter of the bottom edge of the frusto-conical element 58. This column 57 and frusto-conical element 58 cooperate to form a hollow metal reinforcing element that resists the bonding pressure that is applied to the MEMS 22 in the recess 26 by the bonding tool 50. The greater diameter of D2 spreads the wire bonding pressure to an area outside of the centerline of the support carrier, which prevents the support carrier 24 from rotating around its center point, C. Although a frusto-conical element 58 is shown, it will be understood that any other configurations that have a wider base than its top will be suitable for the purpose of spreading the bonding pressure away from the center of the support carrier 24.

The support member may also have an air passage 65 that is formed in its bottom surface to provide a fluid path between the bottom side of the MEMS 22, in instances where the MEMS is a pressure transducer and a pressure source. The passage 65 may mate with a confronting channel 46 formed in the housing of device in which the support carrier 24 is used. (FIG. 10.) This passage 65 runs longitudinally along the support member bottom surface 29, dividing the bottom surface into two side portions 66, which flank the passage 65.

Figure 8:
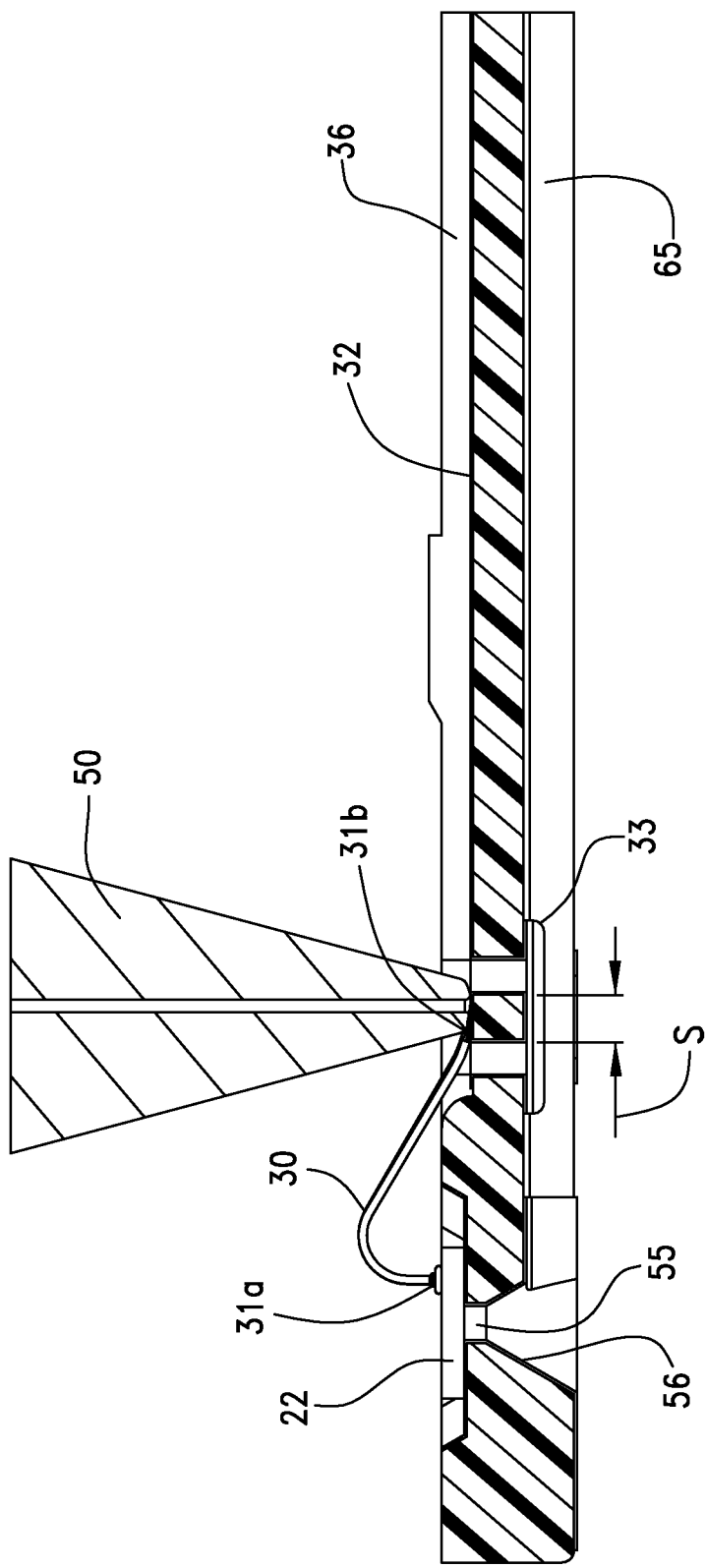
FIG. 8 is the same view as FIG. 7, but with a wire bonding head in contact therewith for bonding one end of a wire to a conductive trace of the support carrier.
Figure 8A:
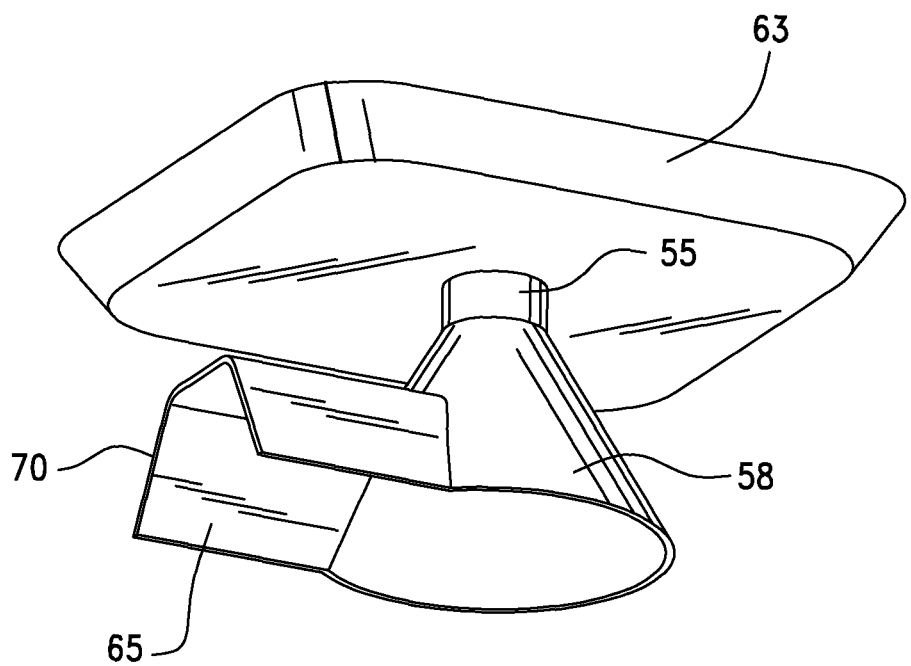
FIG. 8A is a perspective view, taken from the underside of the plated support area, illustrating the microelectronic device support pan and the frusto-conical element connected to the support pan.
Figure 8B:
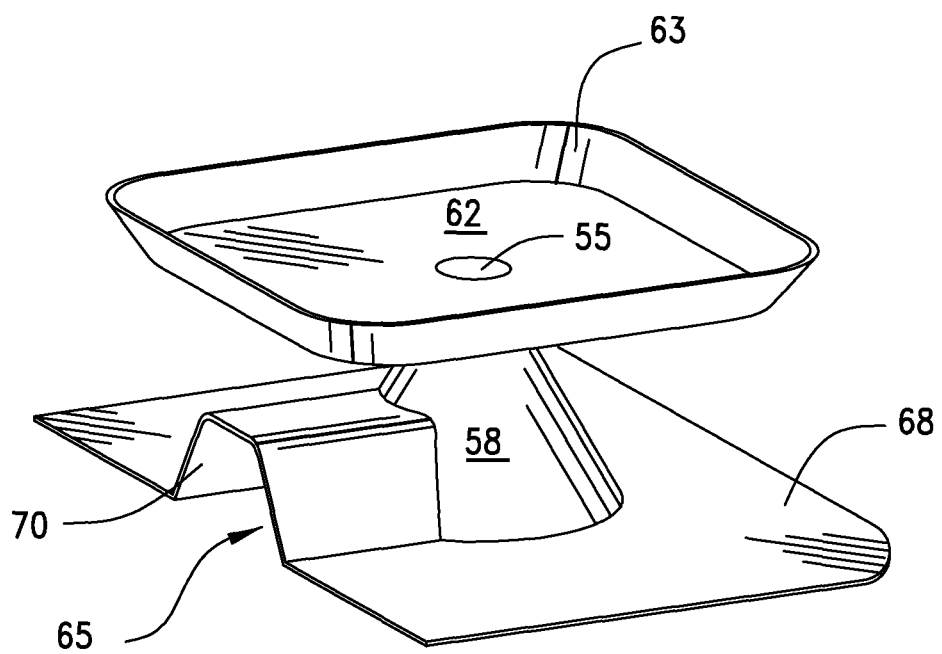
FIG. 8B is the same view as FIG. 8A, but taken from above, looking downward on the support pan, and illustrating the planar support base that extends around the perimeter of the frusto-conical element.
Figure 9:
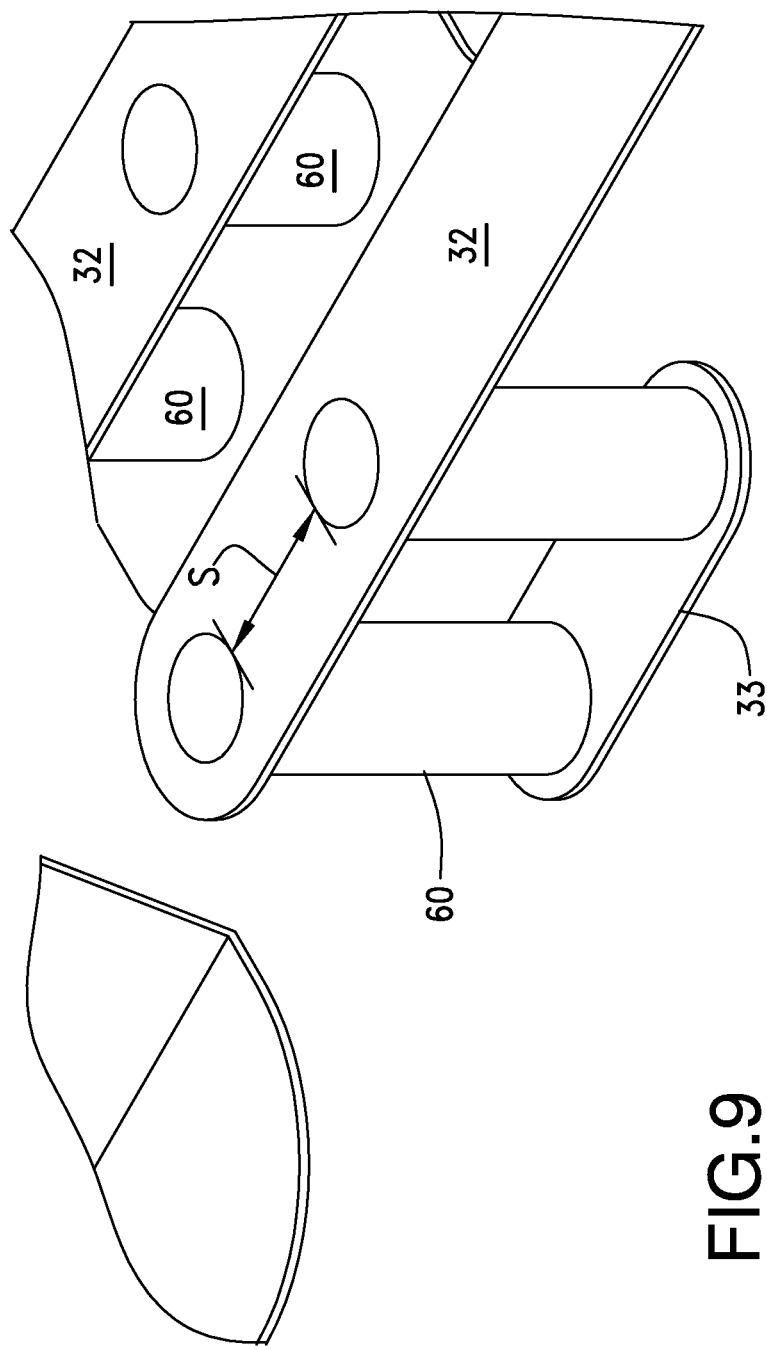
FIG. 9 is an enlarged detail view of the plated columns utilized with one of the conductive traces of the support carrier.

The passage, as best shown in FIG. 8B communicates with the frusto-conical element 58 and a portion of this area is also etched with the laser so as to form a hollow plated frame 70 that has a truncated, generally inverted V-shape. This frame is positioned under the first recess 26 and specifically the area where the wire bonding occurs on the MEMS, i.e. underneath the front of the recess 26. The inverted V-shape assists in spreading out the forces imparted to the MEMS to the sides of the support carrier 24. In addition, the inverted V-shape helps resist rotation of the frusto-conical element.

The bottom side portions 66 and the ribs 39 are, in effect, raised elements that flank or partially surround the plated areas, namely, the conductive traces 32, the recess 26, the holes and the frusto-conical element 58. These raised elements primarily serve as a collision barrier to prevent other parts in the agitated plating solution from colliding with the plated portions on the support member 24, and this reduction or elimination of contact with the traces reduces the possibility that the traces may become abraded and ultimately degraded during the plating process. Secondly, the grooves 36 defined between the raised ribs 39 also improve the plating process, for the plating solution will tend to dwell a longer time in these grooves 36 during the plating process and ensure adherence of the plating material to the excited traces. The raised elements protect the traces from abrasion, and are portions of the support member that are intended to collide with other parts in the plating solution. Thus the agitation speed during the plating process may be increased and there is little concern as to plating material depositing on the ribs for due to their height they are subject to abrasion which will reduce any likelihood of errant plating deposition thereon. This structure is explained in U.S. patent application Ser. No. 12/340,144, filed Dec. 19, 2008 for Plated Dielectric Frame With Integrated Connector, the disclosure of which is hereby incorporated herein by reference in its entirety.

Returning to FIG. 5C, the bottom surface 29 of the support carrier 24 may be plated to form a substantially planar metal layer that forms a base plate 68, which preferably extends widthwise to a distance on opposite sides of the centerline to a distance past the centerlines of any respective outer conductive traces 32. As shown in FIG. 5C, the base plate 68 has a wide, flat surface that bears against a work base upon which the support member is placed during wire bonding, and it counteracts any torque force that may be imparted to the support carrier 24 when the bonding tool 50 contact on one of the outer traces 32 as shown. The plate 68 can provide resistance to rotation of the support carrier 24.

Lastly, other columnar arrangements may be utilized in processes of the present invention. FIG. 12A illustrates the use of a single column 60 where the wire bonding location is located adjacent (within 0.5 mm) to the column, while FIG. 12B illustrates the use of a single column where the wire bonding occurs directly at the top of the column, around the perimeter of the hole. In the latter instance the bonding will close off the top of the column. FIG. 13A illustrates a wider groove 36 that has three holes drilled in it to form tree columns 60. In this application the wire bonding area "WB" is preferably located within the perimeter of an imaginary figure (a triangle) 75 drawn connecting the columns together. FIG. 13B is illustrative of the use of four columns that surround the wire bonding area WB. As can be appreciated, the configuration of the support structure may vary depending on the material properties of the carrier (and the thickness of the plating).

It should be noted that while laser etching is a suitable method of preparing a material to accept a plating, other methods such as chemical etching and the like can also be used. The advantage of using laser etching in combination with a LCP material is that a relatively complex structure can be formed and then selectively laser etched so that plating is applied in the desired locations, potentially reducing the manufacturing steps needed to produce the final assembly.

The disclosure provided herein describes features in terms of preferred and exemplary embodiments thereof. Numerous other embodiments, modifications and variations within the scope and spirit of the appended claims will occur to persons of ordinary skill in the art from a review of this disclosure.

The invention claimed is:

1. A support carrier, comprising:
a support member, the support member formed of a material with a compressive strength of less than 50 MPa at one percent deflection, the support member including a first side and an opposing second side, the first side including a support area for supporting the microelectronic device and a termination area, the support area having a conductive floor disposed for contacting the microelectronic device and the termination area having a conductive trace disposed thereon, the conductive trace and conductive floor being spaced apart from each other;
a first support structure extending from the second side to the conductive trace, the first support structure comprising a metal plating formed on an aperture in the support member, wherein the support structure substantially increases a compressive strength of the support carrier at the termination area; and
a second support structure disposed beneath the conductive floor, the second support structure comprising a plating on a cavity that extends from the second side to the conductive floor.

2. The support carrier of claim 1, wherein the second support structure has a general frusto-conical configuration.

3. The support carrier of claim 1, further including an additional metal layer plated on a second surface of the support member, the additional metal layer having the form of a flat plate extending at least partially around a second end.

4. The support carrier of claim 1, further including an inverted V-shaped hollow frame member communicating with the reinforcement member.

5. The support carrier of claim 4, wherein the frame member is aligned with one of the conductive traces.

6. The support carrier of claim 1, wherein the support member further include a plurality of channels formed in a surface thereof, each of the channels containing a single one of the conductive traces therein.

7. The support carrier of claim 6, wherein the channels extend lengthwise along the support member and a pair of holes are spaced apart from each other lengthwise within the conductive trace.

8. The support carrier of claim 7, wherein the support member further includes conductive traces disposed on a bottom surface of the support member interconnecting bottom ends of the pairs of columns together formed in the holes when plated.

9. The support carrier of claim 7, wherein each of the pairs of holes include a third hole, the three holes arranged at apexes of an imaginary triangle, the three holes defining three hollow metal columns when plated.

10. The support carrier of claim 7, further including an additional pair of holes associated with each pair of holes, the four holes being arranged at apexes of an imaginary four-sided figure, the four holes defining four hollow metal columns when plated.

11. A support system, comprising:
- a support member, the support member formed of a plateable plastic with a compressive strength, the support member including a first side and an opposing second side and an aperture extending between the first side and the second side, the first side including a support area for supporting a microelectronic device and a termination area, the support area having a conductive floor for contacting the microelectronic device and the termination area having a conductive trace disposed thereon, the conductive trace and conductive floor being spaced apart from each other; and
- a support structure extending from the second side to the conductive trace, the first support structure comprising a metal plating formed on the aperture in the support member and a plated base, the metal plating on the aperture forms a first column that extends between the plated base and the conductive trace, the first column providing a first opening in the conductive trace, wherein the support structure increases the compressive strength at one percent deflection of the support carrier at the termination area by at least a factor of four (4).

12. The connector of claim 11, wherein the support structure increases the compressive strength at the termination area by at least a factor of ten (10).

13. The connector of claim 11, wherein the support structure further comprises a second column provided on a second aperture, the second column extending between the plated base and the conductive trace and providing a second opening in the conductive trace, wherein the termination area is positioned between the first and second opening.

14. The connector of claim 11, wherein the support structure is configured to prevent more than five (5) percent deformation of the support member at the termination area when a wire-bond is applied to the termination area.

\* \* \* \* \*